(12) United States Patent
Plank et al.

(10) Patent No.: US 6,653,093 B1
(45) Date of Patent: Nov. 25, 2003

(54) ACCELERATED STABILITY TEST

(75) Inventors: Peter F. Plank, Pacifica, CA (US); Thomas P Graycar, Pacifica, CA (US); Matthew J. Flynn, Mountain View, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/581,561

(22) PCT Filed: Dec. 21, 1998

(86) PCT No.: PCT/US98/27213

§ 371 (c)(1), (2), (4) Date: Jun. 13, 2000

(87) PCT Pub. No.: WO99/31959

PCT Pub. Date: Jul. 1, 1999

Related U.S. Application Data

(60) Provisional application No. 60/070,303, filed on Dec. 20, 1997.

(51) Int. Cl.[7] ................................................ C12Q 1/34
(52) U.S. Cl. ............... 435/18; 252/186.38; 510/392
(58) Field of Search ...................... 435/18, 175, 183, 435/187, 264; 252/186.27, 186.38; 510/221, 372, 375, 376, 378, 392, 530

(56) References Cited

U.S. PATENT DOCUMENTS

| | | | |
|---|---|---|---|
| 3,764,542 A | * 10/1973 | Natali et al. ................. 252/135 |
| 4,261,868 A | 4/1981 | Hora et al. ................... 252/529 |
| 4,404,128 A | 9/1983 | Anderson ..................... 252/546 |
| 4,760,025 A | 7/1988 | Estell et al. .................. 435/222 |
| 5,204,015 A | 4/1993 | Caldwell et al. ........ 252/174.12 |
| 5,254,287 A | * 10/1993 | Deleeuw et al. ........ 252/186.27 |
| 5,324,649 A | 6/1994 | Arnold et al. ............... 435/187 |
| 5,739,091 A | * 4/1998 | Kiesser et al. .............. 510/224 |
| 6,136,772 A | * 10/2000 | DeLima et al. ............. 510/392 |

FOREIGN PATENT DOCUMENTS

| | | |
|---|---|---|
| EP | 0 130 756 B1 | 2/1991 |
| WO | 91 06637 | 5/1991 |
| WO | WO 94 04665 | 3/1994 |

OTHER PUBLICATIONS

Copy of PCT Search Report for US/27213.

* cited by examiner

Primary Examiner—Ralph Gitomer
(74) Attorney, Agent, or Firm—Genencor International, Inc.

(57) ABSTRACT

Enzyme granulates contain besides the enzyme water-soluble and water-insoluble fillers, binders and if required other additives for granulates. In order to stabilize the enzyme, an alkaline or earth alkaline metal formiate is added, as well as reducing sugar, if required. These enzyme granulates may contain all usual enzymes for washing and cleaning purposes, in particular alkaline proteases. A process for preparing these enzyme granulates, as well as their use in powdery washing product compositions are also disclosed.

15 Claims, 1 Drawing Sheet

ACCELERATED STABILITY TEST

This application claims the benefit of Provisional Application No. 60/070,303, filed Dec. 20, 1997.

BACKGROUND OF THE INVENTION

The stability of enzyme granules formulated into bleach-containing detergents is generally excellent—in most cases, showing no more than about 10 to 20% loss in activity over 6 weeks storage at 30 to 37° C. and 70% to 80% R.H. However, to aid in the development and screening of granular formulations, it is desirable to have an accelerated means of determining relative granule stability.

SUMMARY OF THE INVENTION

A method for an accelerated stability test is provided including providing granulated protein; providing a detergent matrix; combining the granulated protein and detergent matrix; incubating the detergent/granule combination for at least one day at high temperature and high humidity; and assaying the sample of the detergent/granule combination. Preferably, the protein is an enzyme.

DETAILED DESCRIPTION OF THE INVENTION

Figure 1:
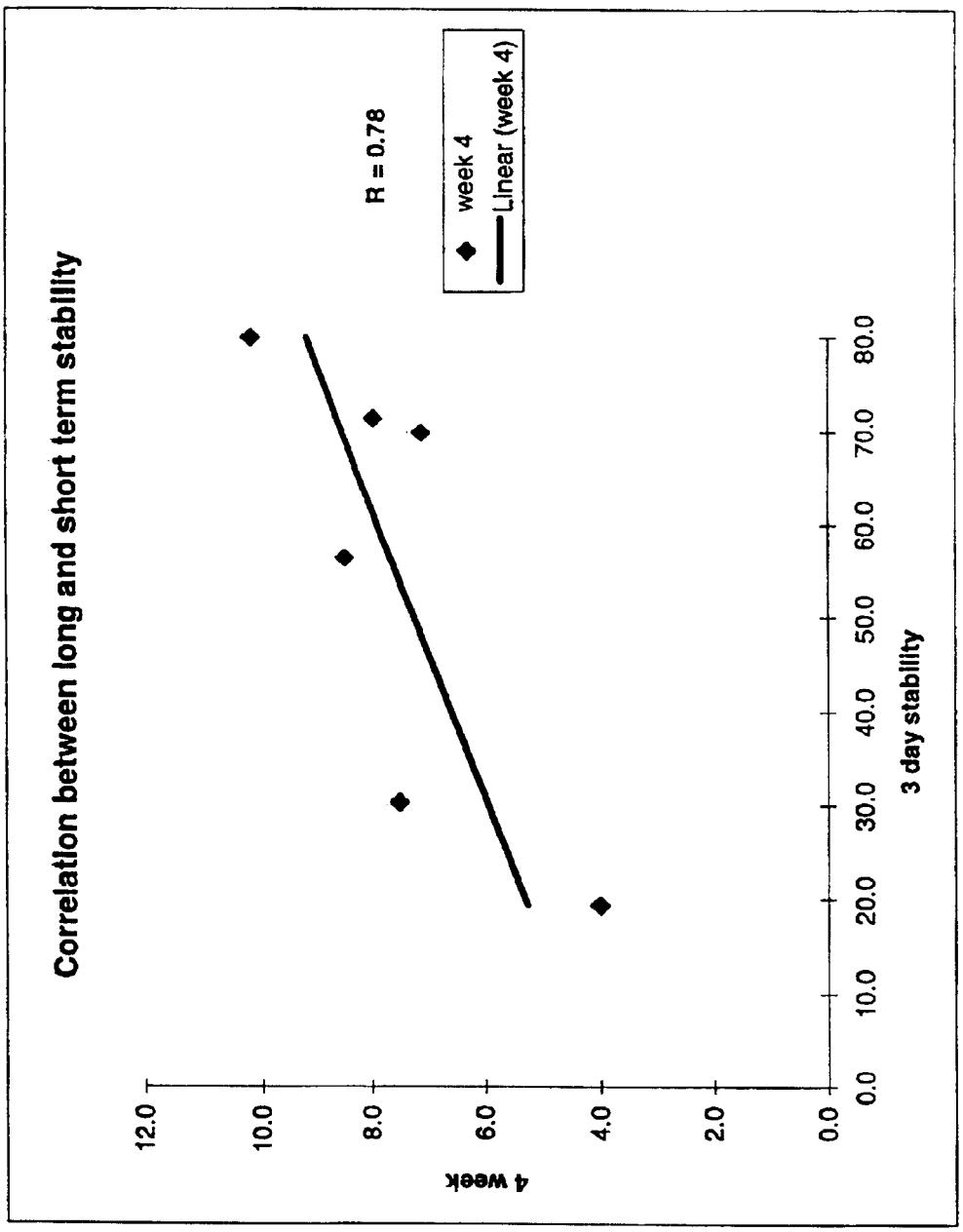
FIG. 1 is a correlation plot showing the correlation between the method iof the present invention and a long term stability study.

The conditions of the method of the present invention are more severe than enzyme granules or detergents would generally encounter in realistic storage or transport. The present method is a "stress test" designed to discriminate differences between granules and formulations in a matter of days which would otherwise not be evident for weeks or months. High temperature and high humidity in combination with a harsh detergent matrix combine to accelerate the appearance of any stability issues that the granule may have and allow for rapid determination of the differences between granules and detergent formulations.

A method for an accelerated stability test is provided including providing granulated protein; providing a detergent matrix; combining the granulated protein and detergent matrix; incubating the detergent/granule combination for at least one day at high temperature and high humidity; and assaying the sample of the detergent/granule combination.

A preferred embodiment of the invention is the following method. Using an analytical balance weigh out an appropriate amount of each sample of enzyme-containing granules into a conical tube. To each tube add an appropriate amount of detergent base, for example, WFK-1 with 25% perborate monohydrate, +3% TAED. Cap tubes. Disperse enzyme granules in base by inverting the tubes several times. Puncture a small hole in the top of each tube, for example, with a ¹⁄₁₆" drill bit. Place day 1 and day 3 samples in the humidity chamber set at 50° C./70% relative humidity.

Determine enzymatic activity in Day "0" samples. Add enzyme detergent mix to 50 ml conical tubes. For each tube, add 30 ml of 0.25 M Mes pH 5.5+20 ul Catalase HP L5000. Cap tube tightly. Shake tube to dissolve detergent and enzyme. Crack cap to release gas. Place all samples on a rotating mixer and allow to incubate. Check tubes to ensure that they do not leak. Remove an aliquot from the liquid layer of the base/buffer mix.

Generally, the detergent matrix used in the present invention is a harsher version than one would find in a commercial detergent formulation which contains protein granules. The detergent matrix includes, for example, surfactants. A number of known compounds are suitable. These include nonionic, anionic, cationic or zwitterionic detergents, as disclosed in U.S. Pat. No. 4,404,128 to Barry J. Anderson and U.S. Pat. No. 4,261,868 to Jiri Flora, et al. A suitable detergent formulation is that described in Example 7 of U.S. Pat. No. 5,204,015 (previously incorporated by reference). The art is familiar with the different formulations which can be used as detergent compositions or matrices.

The detergent matrix can contain higher than normal levels of certain components such as bleaching agents and/or activators. Bleaching agents include percarbonate or perborate compounds such as sodium perborate monohydrate and are preferably present in an amount greater than 20% of the detergent matrix, more preferably in the range of 20–40% of the detergent matrix. Activators include TAED and are preferably present in an amount greater than 5% of the detergent matrix, more preferably in the range of 5–15% of the detergent matrix.

If the detergent base already contains a bleaching agent and/or activator, I may not be necessary to add any additional bleaching agents or activators. In that case, the adverse environmental conditions (temperature and humidity) are sufficient to allow differentiation between the samples.

The temperature and humidity at which the detergent/granule combination is maintained are very important to the present invention. The preferred range of temperatures are 45° C. to 60° C., more preferably, the temperature is about 50° C. For the humidity at which the combination is maintained, the preferred range is 60–80%, more preferably, 65–75%, most preferably, about 70%.

The granules to be tested using the present invention may be made by methods known to those skilled in the art of enzyme granulation, including pan-coating, fluid-bed coating, prilling, disc granulation, spray drying, extrusion, centrifugal extrusion, spheronization, drum granulation, high shear agglomeration, or combinations of these techniques. Granules that can be tested include those made as described in U.S. patent application Ser. No. 08/995,457 or U.S. Pat. No. 5,324,649 as well as those described in numerous other patents and publications.

Proteins that are within the scope of the present invention include pharmaceutically important proteins such as hormones or other therapeutic proteins and industrially important proteins such as enzymes.

Any enzyme or combination of enzymes may be used in the present invention. Preferred enzymes include those enzymes capable of hydrolyzing substrates, e.g. stains. These enzymes are known as hydrolases which include, but are not limited to, proteases (bacterial, fungal, acid, neutral or alkaline), amylases (alpha or beta), lipases, cellulases and mixtures thereof. Particularly preferred enzymes are subtilisins and cellulases. Most preferred are subtilisins such as described in U.S. Pat. No. 4,760,025, EP Patent 130 756 B1 and EP Patent Application WO 91/06637, which are incorporated herein by reference, and cellulases such as Multifect L250™ and Puradax™, commercially available from Genencor International. Other enzymes that can be used in the present invention include oxidases, transferases, dehydratases, reductases, hemicellulases and isomerases.

The following examples are representative and not intended to be limiting. One skilled in the art could choose other conditions, granules, and detergent matrices including other detergent formulation components based on the teachings herein.

EXAMPLES

Definitions g/L grams per liter ml—milliliter ppm—parts per million=mg/L rpm=cpm—revolutions per minute=cycles per minute PBS1—sodium perborate monohydrate—compound added to HDPDs for hydrogen peroxide generation TAED—tetraacetylethylenediamine—bleaching system component in HDPDs. TAED produces peracetic acid when reacted with hydrogen peroxide under alkaline conditions.

HDPD—High density powdered detergent

Equipment and Materials

Humidity Chamber set at 50° C./70% relative humidity

Screw top conical tube, 15 ml, 17×120 mm, Sarstedt Inc., Newton, N.C.

Balance: Suitable balance capable of weighing to ±0.0001 grams.

Rotating Mixer: RKVS made by Appropriate Technical Resources, Laurel,Md. 20705

Dilution buffer: 0.25 M MES pH 5.5

Protease Assay Buffer: 0.1 M Tris 8.6+0.005% Tween 80,

Protease substrate, suc-AAPF pNA 100mg/ml in DMSO

Detergent base: WFK-1 with 25% perborate monohydrate+3% TAED

Catalase: CAT HP L5000, made by Genencor International, Inc. (Rochester, N.Y.)

1/16" drill bit

Protease Assay 980 ul of 0.1 M Tris pH 8.6 ul of AAPF protease substrate,

Temp: 25° C./time 0 to 3 min. at 20 second intervals.

A 405 nm on Beckman spectrometer or another suitable spectrometer.

Do 3 replicates for each tube.

EXAMPLE

In this test, a test detergent base is made from the following ingredients:

| 72% | WFK-1 detergent base | (WFK, Forschunginstitut fuer Reinigungstechnologie e.V., Krefeld, Germany) |
| --- | --- | --- |
| 25% | sodium perborate monohydrate | (Degussa Corp., Allendale Park, New Jersey.) |
| 3% | TAED bleach activator (= tetraacetylethylenediamine) | (Warwick International, Mostyn, UK) |

For each enzyme sample to be tested, three identical tubes were prepared by adding 1 gram of the test base and 30 mg of enzyme granules containing protease enzyme to a 15 ml conical tube and mixed by inverting the capped tube 5–8 times by hand. A hole was drilled in the tube cap with a 1/16 inch drill bit. One of the three tubes was assayed immediately and the other two were stored in a humidity chamber set at 50° C. and 70%R.H. One of the two stored tubes was assayed after 1 day of storage; the second, after 3 days of storage. Storage stability was reported for Day 1 and Day 3 by dividing the remaining activity by the original activity at Day 0, expressed as a percentage.

The enzyme activity was determined by adding to each tube 30 ml of 0.25M MES pH 5.5 buffer containing 20 $\mu$l Catalase HP L5000 (Genencor International, Rochester, N.Y.) and incubating for 40 minutes to inactivate the perborate. After this, the enzyme was assayed by adding 10 $\mu$l of the test tube mixture and 10 $\mu$l of sAAPF protease substrate to 980 $\mu$l of 0.1M Tris pH 8.6, then incubating at 25° C. over 3 minutes, and measuring the optical absorbance at 410 nm. The slope of the absorbance vs. time was then multiplied by the dilution factor and the known extinction coefficient for the specific protease to obtain an enzyme activity as concentration in mg/ml.

This method was carried out on several different granules and the results are shown in FIG. 1.

The same granules were assayed using a long term stability testing protocol wherein the granules were placed in the WFK-1detergent formulation to which nothing had been added. The samples were placed in Whirlpak™ bags (Nasco International, Modesto, Calif.) and kept at 37° C. for four weeks. The results of the two tests are shown in Table 1.

TABLE 1

| Sample | Remaining activity at day 3 at 50° C. | Remaining activity at 4 weeks at 37° C. |
| --- | --- | --- |
| A | 19.4 | 4.0 |
| B | 71.4 | 8.0 |
| C | 90.2 | 6.9 |
| D | 30.3 | 7.5 |
| E | 56.5 | 8.5 |
| F | 79.9 | 10.2 |
| G | 61.0 | 19.6 |
| H | 69.9 | 7.1 |

A plot of the correlation of the results is shown in FIG. 1 and indicates a 0.78 correlation.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

What is claimed is:

1. An accelerated stability testing method to determine activity of granulated protein for inclusion in a detergent, the method comprising the following steps:

a) providing granulated protein and a detergent matrix;

b) preparing one or more samples comprising a selected amount of the granulated protein and a selected amount of the detergent matrix;

c) measuring optical absorbance of one of the one or more samples to determine original protein activity;

d) incubating the one or more samples for 3 days or less at about 45–60° C. in a humidity chamber having a humidity of about 60–80%;

e) measuring optical absorbance of the one or more samples at least once during the 3 days or less incubating step to determine remaining protein activity; and f) calculating percent storage stability of the one or more samples by dividing the remaining activity by the original activity.

2. The method of claim 1, wherein the detergent matrix has at least 20% of a bleaching agent.

3. The method of claim 2, wherein the bleaching agent includes a perborate or a percarbonate source.

4. The method of claim 1, wherein the detergent matrix has at least 5% of a bleaching agent activator.

5. The method of claim 1, wherein the protein is an enzyme.

6. The method of claim 1, wherein the humidity is about 70%.

7. The method of claim 1, wherein the temperature is about 50° C.

8. The method of claim 1 wherein determining enzyme activity in step f) comprises measuring optical absorbance over time of a mixture of a protein having a known activity level with at least a portion of the one or more samples.

9. The method of claim 1 wherein step b) further comprises placing a cap having a 1/16 inch hole over each of the one or more samples.

10. An accelerated stability testing method to determine activity of granulated enzyme for inclusion in a detergent, the method comprising the following steps:

a) providing granulated enzyme and a detergent matrix;

b) preparing one or more samples by mixing together a selected amount of the granulated enzyme and a selected amount of the detergent matrix;

c) measuring optical absorbance of one of the one or more samples to determine original enzyme activity;

d) covering the one or more samples with a cap having a hole therethrough;

e) incubating the one or more covered samples for 3 days at about 45–60° C. in a humidity chamber having a humidity of about 60–80%;

f) measuring optical absorbance of the one or more incubating samples at least after 1 and 3 days of incubation to determine remaining enzyme activity; and g) determining percent storage stability of the assayed samples of step f) by dividing the remaining activity by the original activity.

11. The method of claim 10, wherein the detergent matrix has at least 20% of a bleaching agent.

12. The method of claim 11, wherein the bleaching agent includes a perborate or a percarbonate source.

13. The method of claim 10, wherein the detergent matrix has at least 5% of a bleaching agent activator.

14. The method of claim 10, wherein the humidity is about 70%.

15. The method of claim 10, wherein the temperature is about 50° C.

* * * * *

UNITED STATES PATENT AND TRADEMARK OFFICE
CERTIFICATE OF CORRECTION

PATENT NO. : 6,653,093 B1
DATED : November 25, 2003
INVENTOR(S) : Plank et al.

It is certified that error appears in the above-identified patent and that said Letters Patent is hereby corrected as shown below:

Column 4,
Line 59, Claim 1, should read,
d) incubating the one or more samples for at least one day and up to 3 days at about 45-60º C. in a humidity chamber having a humidity of about 60-80%;
Line 62, Claim 1, should read,
e) measuring optical absorbance of the one or more samples at least once during the incubating step to determine remaining protein activity; and Column 5,
Line 13, Claim 8, should read,
The method of claim 1 wherein determining protein activity in step e comprises measuring optical absorbance over time of a mixture of a protein having a known activity level with at least a portion of the one or more samples.

Column 6,
Line 12, Claim 10, should read,
g) determining percent storage stability by dividing the remaining enzyme activity by the original activity.

Signed and Sealed this

Eleventh Day of January, 2005

JON W. DUDAS
*Director of the United States Patent and Trademark Office*